US012583998B2

(12) United States Patent
Usuda et al.

(10) Patent No.: US 12,583,998 B2
(45) Date of Patent: Mar. 24, 2026

(54) FLUORINE-CONTAINING COPOLYMER COMPOSITION AND CROSS-LINKED PRODUCT THEREOF, AND COMPOUND

(71) Applicant: AGC INC., Tokyo (JP)

(72) Inventors: Tsukasa Usuda, Chiyoda-ku (JP); Yoshitomi Morizawa, Chiyoda-ku (JP); Tsuyoshi Kawai, Chiyoda-ku (JP)

(73) Assignee: AGC INC., Tokyo (JP)

( * ) Notice: Subject to any disclaimer, the term of this patent is extended or adjusted under 35 U.S.C. 154(b) by 690 days.

(21) Appl. No.: 17/884,613

(22) Filed: Aug. 10, 2022

(65) Prior Publication Data

US 2022/0396683 A1 Dec. 15, 2022

Related U.S. Application Data

(63) Continuation of application No. PCT/JP2021/004138, filed on Feb. 4, 2021.

(30) Foreign Application Priority Data

Feb. 21, 2020 (JP) ................................ 2020-028034

(51) Int. Cl.

*C08K 5/3415* (2006.01)
*C07D 207/452* (2006.01)
*C08F 116/20* (2006.01)

(52) U.S. Cl.

CPC ........ *C08K 5/3415* (2013.01); *C07D 207/452* (2013.01); *C08F 116/20* (2013.01)

(58) Field of Classification Search

None

See application file for complete search history.

(56) References Cited

U.S. PATENT DOCUMENTS

| | | | | |
|---|---|---|---|---|
| 2007/0208142 | A1* | 9/2007 | Adair | C08F 214/18 525/387 |
| 2012/0010369 | A1 | 1/2012 | Iizuka et al. | |
| 2016/0032039 | A1* | 2/2016 | Shimizu | C08F 259/08 525/276 |
| 2019/0322785 | A1* | 10/2019 | Menyo | C08L 63/00 |

FOREIGN PATENT DOCUMENTS

| | | | | |
|---|---|---|---|---|
| JP | 63-238115 | A | 10/1988 | |
| JP | 6-56936 | A | 3/1994 | |
| JP | 6-122736 | A | 5/1994 | |
| JP | 2009-529070 | A | 8/2009 | |
| JP | 2012-017432 | A | 1/2012 | |
| JP | 2012-180484 | A | 9/2012 | |
| WO | WO-2018129023 | A1 * | 7/2018 | B29C 64/124 |

OTHER PUBLICATIONS

International Search Report issued Apr. 6, 2021 in PCT/JP2021/004138 filed on Feb. 4, 2021, 3 pages.

* cited by examiner

*Primary Examiner* — Anthony J Frost

(74) *Attorney, Agent, or Firm* — Oblon, McClelland, Maier & Neustadt, L.L.P.

(57) ABSTRACT

Provided are a fluorine-containing copolymer composition containing a fluorine-containing copolymer and a fluorine-containing compound having two maleimide groups, and a cross-linked product thereof, and a compound.

11 Claims, No Drawings

FLUORINE-CONTAINING COPOLYMER COMPOSITION AND CROSS-LINKED PRODUCT THEREOF, AND COMPOUND

CROSS-REFERENCE TO RELATED APPLICATION

This application is a Continuation of International Application No. PCT/JP2021/004138, filed Feb. 4, 2021, which claims priority to Japanese Patent Application No. 2020-028034 filed Feb. 21, 2020. Each of the above applications is hereby expressly incorporated by reference, in its entirety, into the present application.

TECHNICAL FIELD

The present disclosure relates to a fluorine-containing copolymer composition and a cross-linked product thereof, and a compound.

BACKGROUND ART

A fluorine-containing copolymer such as a vinylidene fluoride/hexafluoropropylene-based copolymer, a tetrafluoroethylene/propylene-based copolymer, or a tetrafluoroethylene/perfluoro(alkyl vinyl ether)-based copolymer is known as a fluorine-containing copolymer. A cross-linked product to be obtained by cross-linking such a fluorine-containing copolymer is used as rubber.

For example, in Japanese National-Phase Publication (JP-A) No. 2009-529070, it is described that a composition containing a fluorocarbon polymer including a unit derived from a monomer selected from vinylidene fluoride, tetrafluoroethylene, hexafluoropropylene, vinyl ether, or chlorotrifluoroethylene, a radical reaction initiator, a first curing assistant selected from the group consisting of allyl cyanurate, allyl isocyanurate, metallyl cyanurate, and metallyl isocyanurate, and a second curing assistant containing an organic compound having at least one terminal alkene, which is not a constituent of a group of the first curing assistants, is cross-linked. In Japanese National-Phase Publication (JP-A) No. 2009-529070, in a case of cross-linking the fluorocarbon polymer, the triallyl isocyanurate is used as the first curing assistant. In addition, in Japanese National-Phase Publication (JP-A) No. 2009-529070, N, N-m-phenylene bismaleimide is described as the second curing assistant.

In Japanese Patent Application Laid-Open (JP-A) No. 2012-180484, it is described that a compound having two maleimide groups is used as a monomer for manufacturing a polymer.

SUMMARY OF INVENTION

Technical Problem

In a case where the triallyl isocyanurate described in Japanese National-Phase Publication (JP-A) No. 2009-529070 is used as a cross-linking assistant, compression set of a cross-linked product to be obtained is insufficient and required to be further improved. In addition, in a case where the N, N'-m-phenylene bismaleimide described in in Japanese National-Phase Publication (JP-A) No. 2009-529070 is used as a cross-linking assistant, a cross-linking rate tends to be low. In Japanese Patent Application Laid-Open (JP-A) No. 2012-180484, the compound having two maleimide groups is described; however, a cross-linking technology is not described.

The disclosure has been made in consideration of such circumstances, an object of one embodiment of the present invention is to provide a fluorine-containing copolymer composition that can be cross-linked at a high cross-linking rate and obtain a cross-linked product excellent in compression set. In addition, an object of another embodiment of the invention is to provide a cross-linked product that is excellent in the compression set. In addition, an object of still another embodiment of the invention is to provide a novel compound.

Solution to Problem

Specific means for attaining the objects described above include the following aspects.

<1> A fluorine-containing copolymer composition, containing: a fluorine-containing copolymer; and a fluorine-containing compound having two maleimide groups.

<2> The fluorine-containing copolymer composition according to <1>, in which the fluorine-containing compound having two maleimide groups is a compound represented by the following Formula (1):

(1)

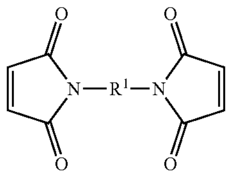

wherein, in Formula (1), 10 is a divalent linking group having from 1 to 30 carbon atoms and a fluorine atom.

<3> The fluorine-containing copolymer composition according to <2>, in which $R^1$ is represented by the following Formula (X):

$$-(L-A)_m-L- \quad (X)$$

wherein, in Formula (X):

m is an integer from 0 to 8, in a case in which m is 0, L is a fluorinated alkylene group having from 1 to 30 carbon atoms, a fluorinated cycloalkylene group having from 3 to 20 carbon atoms, or a fluorinated arylene group having from 5 to 20 carbon atoms, and in a case in which m is 1 or more, each L is independently an alkylene group having from 1 to 30 carbon atoms, a cycloalkylene group having from 3 to 20 carbon atoms, an arylene group having from 5 to 20 carbon atoms, a fluorinated alkylene group having from 1 to 30 carbon atoms, a fluorinated cycloalkylene group having from 3 to 20 carbon atoms, or a fluorinated arylene group having from 5 to 20 carbon atoms, at least one of a plurality of Ls is a fluorinated alkylene group having from 1 to 30 carbon atoms, a fluorinated cycloalkylene group having from 3 to 20 carbon atoms, or a fluorinated arylene group having from 5 to 20 carbon atoms, and each A is independently a single bond or —O—.

<4> The fluorine-containing copolymer composition according to any one of <1> to <3>, wherein in the fluorine-containing compound having two maleimide groups, a number of atoms configuring a main chain linking nitrogen atoms of the two maleimide groups is from 3 to 9.

<5> The fluorine-containing copolymer composition according to any one of <1> to <4>, wherein, in the fluorine-containing compound having two maleimide groups, a fluorine atom content is from 3% by atom to 32% by atom.

<6> The fluorine-containing copolymer composition according to any one of <1> to <5>, wherein the fluorine-containing compound having two maleimide groups is represented by the following Formula (1A) or Formula (1B):

(1A)

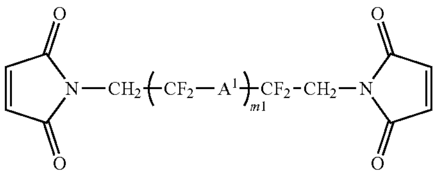

(1B)

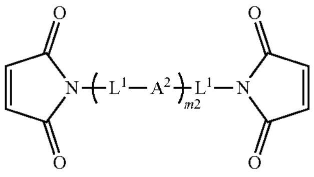

wherein, in Formula (1A), m1 is an integer from 0 to 6, and each $A^1$ is independently a single bond or —O—.
wherein, in Formula (1B), m2 is an integer from 0 to 4, each $L^1$ is independently a perfluoro-o-phenylene group, a perfluoro-m-phenylene group, or a perfluoro-p-phenylene group, and each $A^2$ is independently a single bond or —O—.

<7> The fluorine-containing copolymer composition according to any one of <1> to <6>, wherein the fluorine-containing compound having two maleimide groups is represented by the following Formula (1C) or Formula (1D):

(1C)

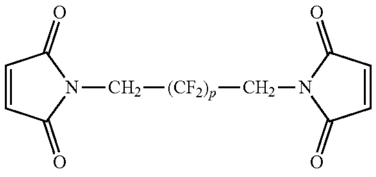

(1D)

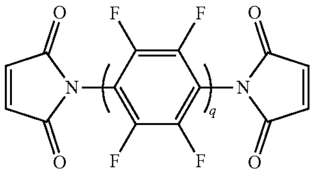

wherein, in Formula (1C), p is an integer from 1 to 7, and wherein, in Formula (1D), q is an integer from 1 to 5.

<8> The fluorine-containing copolymer composition according to any one of <1> to <7>, wherein a ratio of a content of the fluorine-containing compound having two maleimide groups to a content of the fluorine-containing copolymer is from 0.01 to 0.1 on a mass basis.

<9> The fluorine-containing copolymer composition according to any one of <1> to <8>, wherein the fluorine-containing copolymer has an iodine atom and contains a constituent unit derived from tetrafluoroethylene and a constituent unit derived from perfluoroalkyl vinyl ether.

<10> A cross-linked product formed by cross-linking the fluorine-containing copolymer composition according to any one of <1> to <9>.

<11> A compound represented by the following Formula (1A):

(1A)

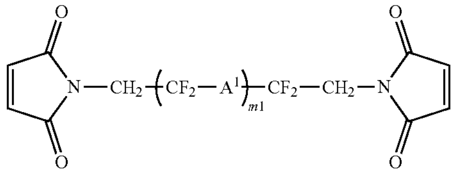

wherein in Formula (1A), m1 is an integer from 0 to 6, and each A' is independently a single bond or —O—.

<12> The compound according to <11>, wherein the compound represented by Formula (1A) is represented by the following Formula (1C):

(1C)

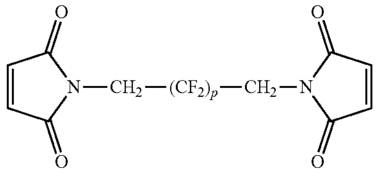

wherein in Formula (1C), p is an integer from 1 to 7.

<13> The compound according to <12>, in which p is 2, 4, or 6.

Advantageous Effects of Invention

According to the disclosure, a fluorine-containing copolymer composition that can be cross-linked at a high cross-linking rate and obtain a cross-linked product excellent in compression set is provided.

In addition, according to the disclosure, a cross-linked product excellent in the compression set is provided.

In addition, according to the disclosure, a novel compound is provided.

DESCRIPTION OF EMBODIMENTS

Hereinafter, a fluorine-containing copolymer composition and a cross-linked product, and a compound of the disclosure will be described in detail.

Herein, a numerical range described by using "to" indicates a range including numerical values before and after "to" as a minimum value and a maximum value, respectively.

Herein, in a case where there are a plurality of substances corresponding to each component in a composition, the amount of each of the components in the composition indicates a total amount of the plurality of substance in the composition, unless otherwise noted.

Herein, a combination of two or more preferred aspects is a more preferred aspect.

Herein, a term "step" includes not only an independent step but also a step that is not capable of being obviously distinguished from the other step insofar as the intended object of the step is attained.

[Fluorine-Containing Copolymer Composition]

A fluorine-containing copolymer composition of the disclosure contains a fluorine-containing copolymer, and a fluorine-containing compound having two maleimide groups.

The fluorine-containing copolymer composition of the disclosure has high compatibility with the fluorine-containing copolymer and the fluorine-containing compound having two maleimide groups, and thus, it is considered that a cross-linking reaction proceeds at a higher cross-linking rate than the related art. In addition, the fluorine-containing compound having two maleimide groups is less likely to be self-polymerized, and thus, it is considered that the cross-linking reaction proceeds at a higher cross-linking rate than the related art. A cross-linked product to be obtained by the cross-linking reaction between the fluorine-containing copolymer and the fluorine-containing compound having two maleimide groups has a more robust cross-linking structure than a cross-linked product of the related art that is obtained by using a cross-linking assistant, and thus, it is considered that the cross-linked product is excellent in compression set.

Hereinafter, each of the component contained in the fluorine-containing copolymer composition of the disclosure will be described.

(Fluorine-Containing Compound Having Two Maleimide Groups)

The fluorine-containing copolymer composition of the disclosure contains the fluorine-containing compound having two maleimide groups. The "fluorine-containing compound" indicates a compound having at least one fluorine atom in the compound.

It is preferable that the fluorine-containing compound having two maleimide groups is a compound represented by Formula (1) described below, from the viewpoint of improving the cross-linking rate and of obtaining the cross-linked product excellent in the compression set.

In Formula (1), $R^1$ is a divalent linking group having from 1 to 30 carbon atoms and a fluorine atom.

It is preferable that $R^1$ is a divalent linking group having at least one fluorine atom, from 1 to 30 carbon atoms, from 0 to 100 hydrogen atoms, from 0 to 10 nitrogen atoms, from 0 to 20 oxygen atoms, and from 0 to 20 sulfur atoms.

Examples of $R^1$ include a group in which at least one hydrogen atom is substituted with a fluorine atom, in one group P selected from the group consisting of a divalent aliphatic group, a divalent aromatic group, and a divalent heterocyclic group, and a group in which at least two groups P are single-bonded. In addition, $R^1$ may be a group in which at least one hydrogen atom is substituted with a fluorine atom, in a group in which at least two groups P selected from the group consisting of a divalent aliphatic group, a divalent aromatic group, and a divalent heterocyclic group are bonded to each other by at least one group Q selected from the group consisting of —O—, —S—, $—SO_2—$, $—NR_L—$, —CO—, —COO—, $—CONR_L—$, $—SO_3—$, and $—SO_2NR_L—$. $R_L$ represents a hydrogen atom or an alkyl group having from 1 to 10 carbon atoms. Among them, it is preferable that the group P is at least one group selected from the group consisting of a divalent aliphatic group and a divalent aromatic group, and it is preferable that the group Q is —O—, from the viewpoint of improving the cross-linking rate and of obtaining the cross-linked product excellent in the compression set.

Examples of the divalent aliphatic group include an alkylene group, an alkenylene group, and an alkynylene group. The divalent aliphatic group may be linear, branched, or cyclic. Among them, it is preferable that the divalent aliphatic group is a linear alkylene group.

Examples of the divalent aromatic group include a phenylene group and a naphthalene group. Among them, it is preferable that the divalent aromatic group is the phenylene group.

It is preferable that a heterocyclic ring configuring the divalent heterocyclic group is a 5-membered ring or a 6-membered ring. The heterocyclic ring may be a monocyclic ring or a concentrated ring. Examples of the heterocyclic ring include a pyridine ring, a piperidine ring, a furane ring, a thiophene ring, a pyrrole ring, a quinoline ring, a morpholine ring, an indole ring, an imidazole ring, a pyrazole ring, a carbazole ring, a phenothiazine ring, a phenoxazine ring, an indoline ring, a thiazole ring, a pyrazine ring, a thiadiazine ring, a benzoquinoline ring, and a thiadiazole ring.

The divalent aliphatic group and the divalent aromatic group may have a substituent. Examples of the substituent include a halogen atom other than a fluorine atom, a cyano group, a nitro group, a hydroxy group, an aliphatic group, an aromatic group, and a heterocyclic group. Examples of the aliphatic group, the aromatic group, and the heterocyclic group include the groups described above.

It is preferable that $R^1$ is represented by Formula (X) described below.

$$-\left(L-A\right)_m-L- \qquad (X)$$

In Formula (X), m is an integer from 0 to 8. In a case where m is 0, L is a fluorinated alkylene group having from 1 to 30 carbon atoms, a fluorinated cycloalkylene group having from 3 to 20 carbon atoms, or a fluorinated arylene group having from 5 to 20 carbon atoms. In a case where m is 1 or more, each L is independently an alkylene group having from 1 to 30 carbon atoms, a cycloalkylene group having form 3 to 20 carbon atoms, an arylene group having from 5 to 20 carbon atoms, a fluorinated alkylene group having from 1 to 30 carbon atoms, a fluorinated cycloalkylene group having from 3 to 20 carbon atoms, or a fluorinated arylene group having from 5 to 20 carbon atoms, at least one of a plurality of Ls is a fluorinated alkylene group having from 1 to 30 carbon atoms, a fluorinated cycloalkylene group having from 3 to 20 carbon atoms, or a fluorinated arylene group having from 5 to 20 carbon atoms, and each A is independently a single bond or —O—.

The "fluorinated alkylene group" indicates an alkylene group in which at least one hydrogen atom that is bonded to a carbon atom is substituted with a fluorine atom. The "fluorinated cycloalkylene group" indicates a cycloalkylene group in which at least one hydrogen atom that is bonded to a carbon atom is substituted with a fluorine atom. The "fluorinated arylene group" indicates an arylene group in which at least one hydrogen atom that is bonded to a carbon atom is substituted with a fluorine atom.

In Formula (X), it is preferable that m is an integer from 0 to 6, in a case where m is 0, it is preferable that L is a fluorinated alkylene group having from 1 to 10 carbon atoms or a fluorinated arylene group having from 5 to 15 carbon atoms, and in a case where m is 1 or more, it is preferable that each L is independently an alkylene group having from 1 to 10 carbon atoms or an arylene group having from 5 to 15 carbon atoms, a fluorinated alkylene group having from 1 to 10 carbon atoms, or a fluorinated arylene group having from 5 to 15 carbon atoms, and at least one of a plurality of Ls is a fluorinated alkylene group having from 1 to 10 carbon atoms or a fluorinated arylene group having from 5 to 15 carbon atoms.

In Formula (X), it is preferable that m is an integer from 0 to 6, in a case where m is 0, it is preferable that L is a perfluoroalkylene group having from 1 to 10 carbon atoms or a perfluoroarylene group having from 5 to 15 carbon atoms, and in a case where m is 1 or more, it is preferable that each L is independently an alkylene group having from 1 to 10 carbon atoms or an arylene group having from 5 to 15 carbon atoms, a perfluoroalkylene group having from 1 to 10 carbon atoms, or a perfluoroarylene group having from 5 to 15 carbon atoms, and at least one of a plurality of Ls is a perfluoroalkylene group having from 1 to 10 carbon atoms or a perfluoroarylene group having from 5 to 15 carbon atoms.

The "perfluoroalkylene group" indicates an alkylene group in which all hydrogen atoms that are bonded to carbon atoms are substituted with fluorine atoms. The "perfluoroarylene group" indicates an arylene group in which all hydrogen atoms that are bonded to carbon atoms are substituted with fluorine atoms.

It is preferable that the fluorine-containing compound having two maleimide groups is represented by Formula (1A) or Formula (1B) described below, from the viewpoint of improving the cross-linking rate and of obtaining the cross-linked product excellent in the compression set.

(1A)

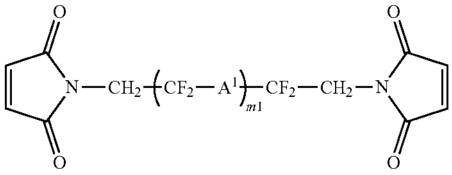

(1B)

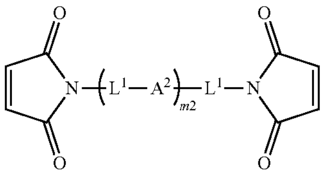

In Formula (1A), m1 is an integer from 0 to 6, and each $A^1$ is independently a single bond or —O—. In Formula (1B), m2 is an integer from 0 to 4, each $L^1$ is independently a perfluoro-o-phenylene group, a perfluoro-m-phenylene group, or a perfluoro-p-phenylene group, and each $A^2$ is independently a single bond or —O—.

In addition, it is preferable that the fluorine-containing compound having two maleimide groups is represented by Formula Formula (1C) or Formula (1D) described below, from the viewpoint of improving the cross-linking rate and of obtaining the cross-linked product excellent in the compression set.

(1C)

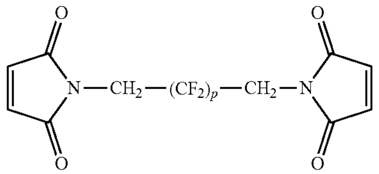

(1D)

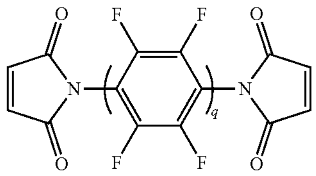

In Formula (1C), p is an integer from 1 to 7. In Formula (1D), q is an integer from 1 to 5.

Specific examples of the fluorine-containing compound having two maleimide groups include the following compounds. Here, the fluorine-containing compound having two maleimide groups in the disclosure is not limited thereto.

A1

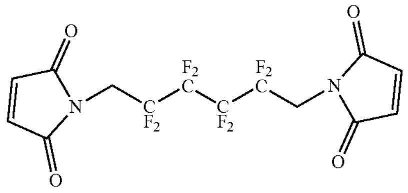

A2

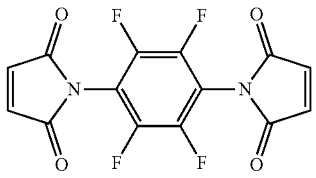

A3

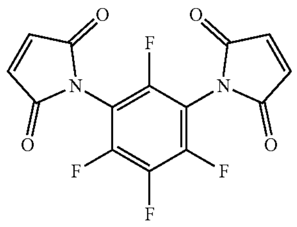

A4

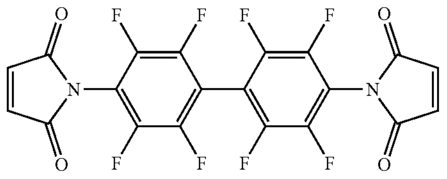

A5

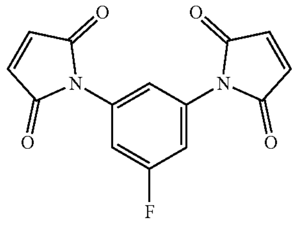

-continued

A6

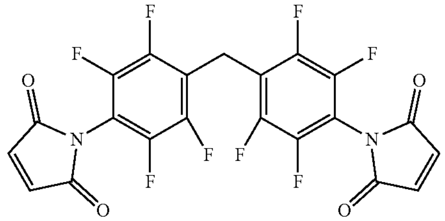

A7

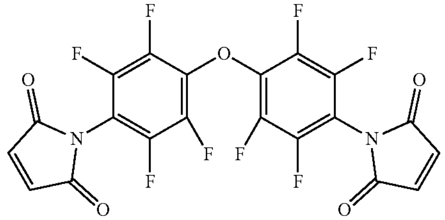

A8

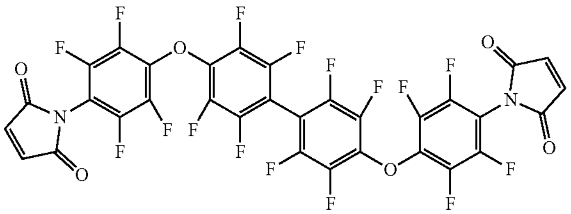

A9

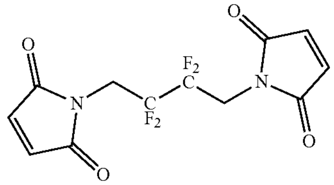

A10

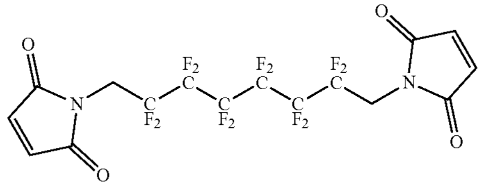

It is preferable that in the fluorine-containing compound having two maleimide groups, the number of atoms configuring a main chain linking nitrogen atoms of two maleimide groups is from 3 to 9. It is more preferable that the number of atoms configuring the main chain linking the nitrogen atoms of two maleimide groups is 4 or more. In addition, it is more preferable that the number of atoms configuring the main chain linking the nitrogen atoms of two maleimide groups is 8 or less. The "number of atoms configuring the main chain linking the nitrogen atoms of two maleimide groups" indicates the number of atoms in a case of following the shortest path between two nitrogen atoms. For example, in the case of the compound A1, the number of atoms configuring the main chain linking the nitrogen atoms of two maleimide groups is 6, and in the case of the compound A2, the number of atoms is 4.

It is preferable that in the fluorine-containing compound having two maleimide groups, a fluorine atom content is from 3% by atom to 32% by atom. The fluorine atom content is more preferably 7% by atom or more, and still more preferably 12% by atom. In addition, the fluorine atom content is more preferably 29% by atom or less, and still more preferably 25% by atom or less. The fluorine atom content can be calculated by analyzing a structure of the fluorine-containing compound with fluorine 19-nuclear magnetic resonance ($^{19}$F-NMR), proton-nuclear magnetic resonance ($^{1}$H-NMR), carbon 13-nuclear magnetic resonance ($^{13}$C-NMR), or the like, and by dividing the number of fluorine atoms in the fluorine-containing compound by the total number of atoms configuring the fluorine-containing compound.

As the fluorine atom content of the compounds described as the specific examples of the fluorine-containing compound having two maleimide groups, A1 is 22% by atom, A2 is 14% by atom, A3 is 14% by atom, A4 is 21% by atom, A5 is 4% by atom, A6 is 20% by atom, A7 is 21% by atom, A8 is 27% by atom, A9 is 13% by atom, and A10 is 29% by atom.

In a case where the fluorine atom content of the fluorine-containing compound having two maleimide groups is in the range described above, the fluorine-containing compound having two maleimide groups has high compatibility with the fluorine-containing copolymer. As a result thereof, the fluorine-containing compound having two maleimide groups and the fluorine-containing copolymer are cross-linked at a higher cross-linking rate. In addition, the self-polymerization between the fluorine-containing compounds having two maleimide groups is less likely to occur, and a cross-linking efficiency is excellent.

The content of the fluorine-containing compound having two maleimide groups is preferably 0.1% by mass or more, more preferably 1% by mass or more, and still more preferably 2% by mass or more, with respect to a total mass of the fluorine-containing copolymer composition, from the viewpoint of improving the cross-linking rate and of obtaining the cross-linked product excellent in the compression set. In addition, the content of the fluorine-containing compound having two maleimide groups is preferably 15% by mass or less, more preferably 10% by mass or less, and still more preferably 7% by mass or less, with respect to the total mass of the fluorine-containing copolymer composition.

(Fluorine-Containing Copolymer)

The fluorine-containing copolymer in the disclosure is not particularly limited insofar as the fluorine-containing copolymer is a copolymer having at least one fluorine atom. Examples of monomers configuring the fluorine-containing copolymer include a fluorine-containing monomer and a hydrocarbon monomer. At least one type of monomers configuring the fluorine-containing copolymer is a fluorine-containing monomer. The fluorine-containing copolymer may contain only one type of constituent unit derived from the fluorine-containing monomer, or may contain two or more types of constituent units in combination. In addition, the fluorine-containing copolymer may contain only one type of constituent unit derived from a hydrocarbon monomer, or may contain two or more types of constituent units in combination.

Examples of the fluorine-containing monomer include tetrafluoroethylene (hereinafter, also referred to as "TFE"), vinylidene fluoride (hereinafter, also referred to as "VDF"), chlorotrifluoroethylene (hereinafter, also referred to as "CTFE"), hexafluoropropylene (hereinafter, also referred to as "HFP"), perfluoroalkyl vinyl ether (hereinafter, also referred to as "PAVE"), a monomer having at least one fluorine atom and two polymerizable unsaturated groups (hereinafter, also referred to as "DVE"), and 2,3,3,3-tetrafluoro-1-propene.

Examples of the hydrocarbon monomer include olefin such as ethylene, propylene, isobutene, or 1-butene.

It is preferable that PAVE is a compound represented by Formula (A), from the viewpoint of improving the cross-linking rate and of obtaining the cross-linked product excellent in the compression set.

$$CF_2{=}CF{-}O{-}R^{f1} \quad (A)$$

In Formula (A), $R^{f1}$ represents a perfluoroalkyl group having from 1 to 10 carbon atoms. The number of carbon atoms of $R^{f1}$ is preferably 8 or less, more preferably 6 or less, still more preferably 5 or less, and particularly preferably 3 or less, from the viewpoint of more excellent polymerization reactivity. In addition, it is preferable that the number of carbon atoms of $R^{f1}$ is 1 or more. The perfluoroalkyl group may be linear or branched.

Examples of PAVE include perfluoro(methyl vinyl ether) (hereinafter, referred to as "PMVE"), perfluoro(ethyl vinyl ether) (hereinafter, also referred to as "PEVE"), perfluoro (propyl vinyl ether) (hereinafter, also referred to as "PPVE"), and perfluoro(methoxy ethyl vinyl ether). Among them, it is preferable that PAVE is PMVE or PPVE, from the viewpoint of more excellent polymerization reactivity.

It is preferable that DVE is a compound represented by Formula (B), from the viewpoint of improving the cross-linking rate and of obtaining the cross-linked product excellent in the compression set.

$$(CR^{21}R^{22}{=}CR^{23})_2R^{24} \quad (B)$$

In Formula (B), each of $R^{21}$, $R^{22}$, and $R^{23}$ independently represents a hydrogen atom, a fluorine atom, a methyl group, or a trifluoromethyl group. $R^{24}$ represents a perfluoroalkylene group having from 1 to 10 carbon atoms, or a group having an etheric oxygen atom on a terminal or in a carbon-carbon bond of the perfluoroalkylene group having from 1 to 10 carbon atoms. A plurality of $R^{21}$s, a plurality of $R^{22}$s, and a plurality of $R^{23}$s may be identical to or different from each other and are preferably identical to each other.

It is preferable that each of $R^{21}$, $R^{22}$, and $R^{23}$ independently represents a fluorine atom or a hydrogen atom, it is more preferable that all of $R^{21}$, $R^{22}$, and $R^{23}$ are a fluorine atom or a hydrogen atom, and it is still more preferable that all of $R^{21}$, $R^{22}$, and $R^{23}$ are a fluorine atom, from the viewpoint of improving the cross-linking rate.

$R^{24}$ may be linear, branched, or cyclic, and is preferably linear or branched, and still more preferably linear. The number of carbon atoms of $R^{24}$ is preferably 2 or more, and more preferably 3 or more. In addition, the number of carbon atoms of $R^{24}$ is preferably 8 or less, more preferably 7 or less, still more preferably 6 or less, and particularly preferably 5 or less.

It is preferable that $R^{24}$ is a group having an etheric oxygen atom on a terminal or in a carbon-carbon bond of a perfluoroalkylene group having from 1 to 10 carbon atoms, from the viewpoint of improving the cross-linking rate. The number of etheric oxygen atoms in $R^{24}$ is preferably 6 or less, and more preferably 3 or less. In addition, it is preferable that the number of etheric oxygen atoms in $R^{24}$ is 1 or more. It is still more preferable that the number of etheric oxygen atoms in $R^{24}$ is 1 or 2. It is preferable that the etheric oxygen atom in $R^{24}$ is on a terminal of $R^{24}$.

It is more preferable that DVE is a compound represented by Formula (C) or a compound represented by Formula (D), from the viewpoint of improving the cross-linking rate and of obtaining the cross-linked product excellent in the compression set.

$$(CF_2{=}CF)_2R^{31} \quad (C)$$

$$(CH_2{=}CH)_2R^{41} \quad (D)$$

In Formula (C), $R^{31}$ represents a perfluoroalkylene group having from 1 to 10 carbon atoms, or a group having an etheric oxygen atom on a terminal or in a carbon-carbon bond of the perfluoroalkylene group having from 1 to 10 carbon atoms.

In Formula (D), $R^{41}$ represents a perfluoroalkylene group having from 1 to 10 carbon atoms, or a group having an etheric oxygen atom on a terminal or in a carbon-carbon bond of the perfluoroalkylene group having from 1 to 10 carbon atoms.

Specific examples of the compound represented by Formula (C) include $CF_2{=}CFO(CF_2)_2OCF{=}CF_2$, $CF_2{=}CFO(CF_2)_3OCF{=}CF_2$, $CF_2{=}CFO(CF_2)_4OCF{=}CF_2$, $CF_2{=}CFO(CF_2)_6OCF{=}CF_2$, $CF_2{=}CFO(CF_2)_8OCF{=}CF_2$, $CF_2{=}CFO(CF_2)_2OCF(CF_3)CF_2OCF{=}CF_2$, $CF_2{=}CFO(CF_2)_2O(CF(CF_3)CF_2O)_2CF{=}CF_2$, $CF_2{=}CFOCF_2O(CF_2CF_2O)_2CF{=}CF_2$, $CF_2{=}CFO(CF_2O)_3(CF(CF_3)CF_2O)_2CF{=}CF_2$, $CF_2{=}CFOCF_2CF(CF_3)O(CF_2)_2OCF(CF_3)CF_2OCF{=}CF_2$, and $CF_2{=}CFOCF_2CF_2O(CF_2O)_2CF_2CF_2OCF{=}CF_2$.

Among the compounds represented by Formula (C), $CF_2{=}CFO(CF_2)_3OCF{=}CF_2$ (hereinafter, also referred to as "C3DVE") or $CF_2{=}CFO(CF_2)_4OCF{=}CF_2$ (hereinafter, also referred to as "C4DVE") is preferable, and C3DVE is more preferable.

Specific examples of the compound represented by Formula (D) include $CH_2{=}CH(CF_2)_2CH{=}CH_2$, $CH_2{=}CH(CF_2)_4CH{=}CH_2$, and $CH_2{=}CH(CF_2)_6CH{=}CH_2$.

Among the compounds represented by Formula (D), $CH_2{=}CH(CF_2)_6CH{=}CH_2$ (hereinafter, also referred to as "C6DV") is preferable.

In a case where DVE is copolymerized with other monomers, a part of a polymerizable double bond on a terminal of DVE reacts during the polymerization, and a branched fluorine-containing copolymer is obtained. The branched fluorine-containing copolymer imparts lower compression set, and is excellent in sealing properties, compared to a linear fluorine-containing copolymer.

The fluorine-containing copolymer in the disclosure may contain constituent units other than the constituent units derived from the monomers described above. Examples of the other constituent units include a constituent unit derived from a compound having a fluorine atom and a nitrile group, a constituent unit derived from perfluorooxyalkyl vinyl ether, and a constituent unit derived from a compound having a fluorine atom and a halogen atom other than the fluorine atom.

It is preferable that the compound having a fluorine atom and a nitrile group is a compound represented by Formula (E).

$$CR^{51}R^{52}{=}CR^{53}{-}R^{54}{-}CN \quad (E)$$

In Formula (E), each of $R^{51}$, $R^{52}$, and $R^{53}$ independently represents a hydrogen atom, a fluorine atom, or a methyl group. $R^{54}$ represents a perfluoroalkylene group having from 1 to 10 carbon atoms, or a group having an etheric oxygen atom on a terminal or in carbon-carbon bond of the perfluoroalkylene group having from 1 to 10 carbon atoms.

It is preferable that each of $R^{51}$, $R^{52}$, and $R^{53}$ independently is a fluorine atom or a hydrogen atom, it is more preferable that all of $R^{51}$, $R^{52}$, and $R^{53}$ are a fluorine atom or a hydrogen atom, and it is still more preferable that all of $R^{51}$, $R^{52}$, and $R^{53}$ are a fluorine atom.

$R^{54}$ may be linear, branched, or cyclic, and is preferably linear or branched, and still more preferably linear. The number of carbon atoms of $R^{54}$ is preferably 2 or more, and more preferably 3 or more. In addition, the number of carbon atoms of $R^{54}$ is preferably 8 or less, more preferably 7 or less, still more preferably 6 or less, and particularly preferably 5 or less.

It is preferable that $R^{54}$ is a group having an etheric oxygen atom on a terminal or in a carbon-carbon bond of a perfluoroalkylene group having from 1 to 10 carbon atoms. The number of etheric oxygen atoms in $R^{54}$ is preferably from 1 to 3, and more preferably 1 or 2. It is preferable that the etheric oxygen atom in $R^{54}$ is on a terminal of $R^{54}$.

Specific examples of the compound represented by Formula (E) include $CF_2{=}CFOCF_2CF(CF_3)OCF_2CF_2CN$, $CF_2{=}CFO(CF_2)_5CN$, $CF_2{=}CFOCF_2CF_2CF_2OCF(CF_3)CN$, and $CF_2{=}CFO(CF_2)_3CN$.

It is preferable that the perfluorooxyalkyl vinyl ether is a compound represented by Formula (F).

$$CF_2{=}CF{-}O{-}R^{f1} \qquad (F)$$

In Formula (F), $R^{f2}$ represents a perfluoroalkyl group having from 1 to 8 carbon atoms and from 1 to 5 etheric oxygen atoms. The number of carbon atoms of $R^{f1}$ is preferably from 1 to 6, and particularly preferably from 1 to 5.

Specific examples of the compound represented by Formula (F) include perfluoro(3,6-di oxa-1-pentene), perfluoro (3,6-di oxa-1-octene), and perfluoro(5-methyl-3,6-di oxa-1-nonene).

It is preferable that the compound having a fluorine atom and a halogen atom other than the fluorine atom is a compound having either an iodine atom or a bromine atom or both of the iodine atom and the bromine atom.

Specific examples of the compound having a fluorine atom and a halogen atom other than the fluorine atom include $CF_2{=}CFBr$, $CH_2{=}CHCF_2CF_2Br$, $CF_2{=}CFOCF_2CF_2I$, $CF_2{=}CFOCF_2CF_2Br$, $CF_2{=}CFOCF_2CF_2CH_2I$, $CF_2{=}CFOCF_2CF_2CH_2Br$, $CF_2{=}CFOCF_2CF(CF_3)$ $OCF_2CF_2CH_2T$, and $CF_2{=}CFOCF_2CF(CF_3)OCF_2CF_2CF_2Br$.

Examples of a fluorine-containing copolymer not containing the constituent unit derived from the hydrocarbon monomer include a TFE/PAVE copolymer, a VDF/HFP copolymer, a TFE/VDF/HFP copolymer, a VDF/HFP/PAVE copolymer, a VDF/CTFE copolymer, and a TFE/PAVE/DVE copolymer. In addition, examples of a fluorine-containing copolymer containing the constituent unit derived from the hydrocarbon monomer include a TFE/propylene copolymer, a TFE/propylene/VDF copolymer, a TFE/propylene/CTFE copolymer, and an ethylene/HFP copolymer.

The fluorine-containing copolymer in the disclosure is preferably at least one type selected from the group consisting of a TFE/PAVE copolymer, a VDF/HFP copolymer, a TFE/VDF/HFP copolymer, a VDF/HFP/PAVE copolymer, a TFE/PAVE/DVE copolymer, a TFE/propylene copolymer, and a TFE/propylene/VDF copolymer, more preferably a TFE/PAVE copolymer, a TFE/PAVE/DVE copolymer, a TFE/propylene copolymer, or a TFE/propylene/VDF copolymer, still more preferably a TFE/PAVE copolymer or a TFE/PAVE/DVE copolymer, and most preferably a TFE/PAVE/DVE copolymer, from the viewpoint of improving the cross-linking rate and of obtaining the cross-linked product excellent in the compression set. That is, the fluorine-containing copolymer in the disclosure preferably contains a constituent unit derived from TFE and a constituent unit derived from PAVE, and more preferably contains a constituent unit derived from TFE, a constituent unit derived from PAVE, and a constituent unit derived from DVE.

The content of the constituent unit derived from TFE is preferably 50% by mole or more, more preferably 60% by mole or more, and still more preferably 63% by mole or more, with respect to a total mass of the fluorine-containing copolymer, from the viewpoint of improving the cross-linking rate and of obtaining the cross-linked product excellent in the compression set. In addition, the content of the constituent unit derived from TFE is preferably 81% by mole or less, more preferably 79% by mole or less, and still more preferably 77% by mole or less.

The content of the constituent unit derived from PAVE is preferably 19% by mole or more, more preferably 21% by mole or more, and still more preferably 23% by mole or more, with respect to the total mass of the fluorine-containing copolymer, from the viewpoint of improving the cross-linking rate and of obtaining the cross-linked product excellent in the compression set. In addition, the content of the constituent unit derived from PAVE is preferably 50% by mole or less, more preferably 40% by mole or less, and still more preferably 37% by mole or less.

The content of the constituent unit derived from DVE is preferably 0.01% by mole or more, more preferably 0.03% by mole or more, and still more preferably 0.05% by mole or more, with respect to the total mass of the fluorine-containing copolymer, from the viewpoint of improving the cross-linking rate and of obtaining the cross-linked product excellent in the compression set. In addition, the content of the constituent unit derived from DVE is preferably 1.0% by mole or less, more preferably 0.6% by mole or less, and still more preferably 0.03% by mole or less.

The content of the constituent unit derived from DVE is calculated on the basis of the amount of DVE that is used in a case of manufacturing the fluorine-containing copolymer (a used amount of DVE). Here, the "used amount of DVE" is a value obtained by subtracting the amount of unpolymerized DVE from the amount of DVE added to a polymerization vessel (a prepared amount of DVE). It is considered that the unpolymerized DVE is contained in a filtrate after aggregating latex after the polymerization and taking out the fluorine-containing copolymer, and in a filtrate remaining after washing the latex. For example, fluoride ions in the filtrate are measured with an ion chromatograph measuring device, and thus, the amount thereof can be measured.

In addition, the content of the constituent unit derived from TFE and the content of the constituent unit derived from PAVE are calculated by using fluorine 19-nuclear magnetic resonance ($^{19}F$-NMR). Specifically, a molar ratio of the constituent unit derived from TFE and the constituent unit derived from PAVE in the fluorine-containing copolymer is calculated by the fluorine 19-nuclear magnetic resonance ($^{19}F$-NMR). Then, the content of the constituent unit derived from TFE and the content of the constituent unit derived from PAVE are calculated on the basis of a value obtained by subtracting the content (% by mole) of the constituent unit derived from DVE from 100% by mole, and the molar ratio described above.

The fluorine-containing copolymer preferably has an iodine atom or a bromine atom and more preferably has an iodine atom. The iodine atom or the bromine atom functions as a cross-linking point that reacts with the fluorine-containing compound having two maleimide groups.

In a case of manufacturing the fluorine-containing copolymer, the iodine atom or the bromine atom can be introduced into the fluorine-containing copolymer by using an iodine compound or a bromo compound as a chain transfer agent described below. In addition, the iodine atom or the bromine atom can be introduced into the fluorine-containing copolymer by copolymerizing a compound having an iodine atom or a bromine atom with other monomers.

The content of the iodine atom or the bromine atom is preferably 0.01% by mass or more, and more preferably 0.05% by mass or more, with respect to the total mass of the fluorine-containing copolymer. In addition, the content of the iodine atom or the bromine atom is preferably 5.0% by mass or less, more preferably 2.0% by mass or less, and still more preferably 1.0% by mass or less. In a case where the content of the iodine atom or the bromine atom is in the range described above, the cross-linking rate can be higher, and the cross-linked product more excellent in the compression set can be obtained.

It is preferable that the fluorine-containing copolymer has an iodine atom and contains the constituent unit derived from TFE and the constituent unit derived from PAVE.

A storage elastic modulus G' of the fluorine-containing copolymer is preferably 450 kPa or more, and more preferably 470 kPa or more. In a case where the storage elastic modulus G' is 450 kPa or more, the cross-linked product more excellent in the compression set can be obtained.

The storage elastic modulus G' of the fluorine-containing copolymer is preferably 650 kPa or less, more preferably 630 kPa or less, and still more preferably 600 kPa or less, from the viewpoint of workability.

The storage elastic modulus G' is an indication of an average molecular weight, in a case where the storage elastic modulus is high, the molecular weight is large, and in a case where the storage elastic modulus is low, the molecular weight is small. The storage elastic modulus G' is a value to be measured on the basis of ASTM D5289 and ASTM D6204. The storage elastic modulus G', for example, is measured by using a dynamic viscoelastic device (Product Name "RPA2000", manufactured by Alpha Technologies) in a condition of a temperature of 100° C., an amplitude of 0.5 degrees, and a vibration frequency of 50 times/minute.

For the details of components other than the components described above that are used in a case of manufacturing the fluorine-containing copolymer and a method of manufacturing the fluorine-containing copolymer, it is possible to refer to a method described in Paragraphs 0019 to 0034 of International Publication No. 2010/082633.

It is preferable that a ratio of the content of the fluorine-containing compound having two maleimide groups to the content of the fluorine-containing copolymer is from 0.01 to 0.1 on a mass basis. The ratio described above is more preferably 0.02 or more, and still more preferably 0.03 or more, on a mass basis. In addition, the ratio described above is more preferably 0.08 or less, and still more preferably 0.07 or less, on a mass basis.

(Other Components)

The fluorine-containing copolymer composition of the disclosure may contain at least one type selected from the group consisting of a cross-linking agent and a catalyst, in addition to the fluorine-containing copolymer and the fluorine-containing compound having two maleimide groups.

Examples of the cross-linking agent include an organic peroxide, polyol, and polyamine. It is preferable that the fluorine-containing copolymer composition of the disclosure contains the cross-linking agent, from the viewpoint of obtaining the cross-linked product excellent in the compression set. It is preferable that the cross-linking agent is an organic peroxide, from the viewpoint of improving the cross-linking rate.

Examples of the organic peroxide include a dialkyl peroxide, α,α'-bis(tert-butyl peroxy)-p-diisopropyl benzene, α,α'-bis(tert-butyl peroxy)-m-diisopropyl benzene, benzoyl peroxide, tert-butyl peroxybenzene, and 2,5-dimethyl-2,5-di(benzoyl peroxy)hexane.

Examples of the dialkyl peroxide include 1,1-di(tert-butyl peroxy)-3,3,5-trimethyl cyclohexane, 2,5-dimethyl hexane-2,5-dihydroxyperoxide, tert-butyl cumyl peroxide, dicumyl peroxide, 2,5-dimethyl-2,5-di(tert-butyl peroxy)hexane, 2,5-dimethyl-2,5-di(tert-butyl peroxy)-3-hexine, a tert-butyl peroxymaleic acid, and diisopropyl peroxydicarbonate.

In a case where the fluorine-containing copolymer composition contains the cross-linking agent, the content of the cross-linking agent is preferably 0.3 parts by mass or more, and more preferably 0.5 parts by mass or more, with respect to 100 parts by mass of the fluorine-containing copolymer. In addition, the content of the cross-linking agent is preferably 10 parts by mass or less, more preferably 5 parts by mass or less, and still more preferably 3 parts by mass or less. In a case where the content of the cross-linking agent is in the range described above, the cross-linked product to be obtained has an excellent balance between strength and elongation.

Examples of the catalyst include an organic tin compound. Examples of the organic tin compound include tin tetramethyl, tin tetra(n-butyl), and tin tetraphenyl.

In a case where the fluorine-containing copolymer composition contains the catalyst, the content of the catalyst is preferably 0.3 parts by mass or more, and more preferably 0.5 parts by mass or more, with respect to 100 parts by mass of the fluorine-containing copolymer. In addition, the content of the catalyst is preferably 10 parts by mass or less, more preferably 5 parts by mass or less, and still more preferably 3 parts by mass or less. In a case where the content of the catalyst is in the range described above, the cross-linked product to be obtained has an excellent balance between the strength and the elongation.

The fluorine-containing copolymer composition may further contain components other than the components described above, within a range not impairing the effects of the disclosure. Examples of the other components include a cross-linking assistant (for example, triallyl cyanurate, triallyl isocyanurate, and trimetallyl isocyanurate), an acid-acceptor (for example, fatty acid ester, a fatty acid metal salt, and an oxide of a divalent metal (magnesium oxide, calcium oxide, zinc oxide, lead oxide, or the like)), a filler and a reinforcing material (for example, carbon black, barium sulfate, calcium metasilicate, calcium carbonate, titanium oxide, silicon dioxide, clay, and talc), a scorch retarder (for example, a phenolic hydroxyl group-containing compound such as bisphenol A; a quinone such as hydroquinone; and an α-methyl styrene dimer such as 2,4-di(3-isopropyl phenyl)-4-methyl-1-pentene), crown ether (for example, 18-crown-6), and a mold-releasing agent (for example, sodium stearate).

In a case where the fluorine-containing copolymer composition contains the other components, a total content of the other components is preferably greater than 0 parts by mass, more preferably 1 part by mass or more, and still more preferably 5 parts by mass or more, with respect to 100 parts by mass of the fluorine-containing copolymer. In addition, the total content of the other components is preferably 30 parts by mass or less, more preferably 25 parts by mass or less, and still more preferably 15 parts by mass or less.

Examples of a method of preparing the fluorine-containing copolymer composition include a method of mixing each of the components described above. Each of the components can be mixed by using a mixing device for a rubber, such as a roll, a kneader, a Banbury mixer, or an extruder.

In addition, a mixture is obtained by mixing each of the components described above, and then, the mixture may be molded. Examples of a method of molding the mixture include compression molding, injection molding, extrusion molding, calender molding, and a method of molding the mixture by dissolving the mixture in a solvent and by dipping a substrate or the like in the solvent or coating the substrate with the solvent.

[Cross-Linked Product]

The cross-linked product of the disclosure is a cross-linked product in which the fluorine-containing copolymer in the fluorine-containing copolymer composition described above is cross-linked.

Examples of a method of cross-linking the fluorine-containing copolymer in the fluorine-containing copolymer composition include a method using heating and a method using radiation irradiation, and a method of cross-linking the fluorine-containing copolymer composition by heating is preferable.

Examples of the cross-linking method using heating include heating press cross-linking, steam cross-linking, and hot-air cross-linking. The cross-linking method may be selected as appropriate, in consideration of the shape of the fluorine-containing copolymer composition, the application of the cross-linked product, and the like.

A heating condition is preferably from 1 second to 24 hours at from 100° C. to 400° C.

The fluorine-containing copolymer composition may be heated (subjected to primary cross-linking), and then, may be subjected to secondary cross-linking by being further heated. By performing the secondary cross-linking, mechanical properties, the compression set, and other properties of the cross-linked product to be obtained can be improved.

A heating condition in a case of performing the secondary cross-linking is preferably from 30 minutes to 48 hours at from 80° C. to 350° C.

Examples of a method of cross-linking the fluorine-containing copolymer by other than the heating include a method of cross-linking the fluorine-containing copolymer by irradiating the fluorine-containing copolymer composition with a radioactive ray. Examples of the radioactive ray to be irradiated include an electron ray and an ultraviolet ray.

A hardness (Shore-A) of the cross-linked product is preferably 65 or more, more preferably 68 or more, and still more preferably 70 or more, from the viewpoint of being excellent in rubber properties. In addition, the hardness (Shore-A) of the cross-linked product is preferably 100 or less, more preferably 90 or less, and still more preferably 85 or less.

The hardness (Shore-A) of the cross-linked product is a value to be measured by using a plate-shaped molded product (a thickness of 1 mm) of the cross-linked product and by using a type A durometer, on the basis of JIS K6253-3:2012.

A tensile strength (a tensile break strength) of the cross-linked product is preferably 1 MPa or more, and more preferably 5 MPa or more, from the viewpoint of being excellent in the rubber properties. In addition, the tensile strength (the tensile break strength) of the cross-linked product is preferably 50 MPa or less, and more preferably 35 MPa or less.

A tensile elongation (a breaking elongation rate) of the cross-linked product is preferably 100% or more, and more preferably 120% or more, from the viewpoint of being excellent in the rubber properties. In addition, the tensile elongation (the breaking elongation rate) of the cross-linked product is preferably 1000% or less, and more preferably 600% or less.

The tensile strength and the tensile elongation of the cross-linked product are a value to be measured by a method based on JIS K 6251:2010 (corresponding International Standard ISO 37:2005).

The compression set of the cross-linked product after being retained at 250° C. for 70 hours is preferably 70% or less, and more preferably 65% or less, from the viewpoint that the fluorine-containing copolymer is cross-linked favorably and a shape recovery is excellent after pressurizing the cross-linked product.

The compression set of the cross-linked product after being retained at 250° C. for 168 hours is preferably 85% or less, and more preferably 82% or less, from the viewpoint that the fluorine-containing copolymer is cross-linked favorably and the shape recovery is excellent after pressurizing the cross-linked product.

The compression set of the cross-linked product after being retained at 250° C. for 336 hours is preferably 97% or less, and more preferably 93% or less, from the viewpoint that the fluorine-containing copolymer is cross-linked favorably and the shape recovery is excellent after pressurizing the cross-linked product.

It is preferable that a lower limit value of the compression set of the cross-linked product after being retained at 250° C. for 70 hours is 0%, and it is more preferable that the compression set of the cross-linked product after being retained at 250° C. for 70 hours is 0%.

The compression set of the cross-linked product is a value to be measured on the basis of JIS K 6262:2013. Here, a test piece in a case of measuring the compression set is an O-ring test piece of P26 of JIS B 2401-1:2012.

Each of the physical properties of the cross-linked product, for example, can be adjusted in accordance with the manufacturing condition of the fluorine-containing copolymer (for example, an addition order, the number of times for addition, and an addition amount of each of the monomers), the type and the content of each of the components contained in the fluorine-containing copolymer composition, and a manufacturing condition of a cross-linking rubber body (for example, a cross-linking condition).

The cross-linked product of the disclosure is preferable for the material of an O-ring, a sheet, a gasket, an oil seal, a diaphragm, a V-ring, or the like. In addition, the cross-linked product of the disclosure can also be applied a to heat-resistant and chemical-resistant seal material, a heat-resistant and oil-resistant seal material, wire coating material, a seal material for a semiconductor device, corrosion-resistant rubber coating material, a urea-based grease-resistant seal material, a rubber coating material, an adhesive rubber, a hose, a tube, a calender sheet (a roll), a sponge, a rubber roll, an oil-drilling member, a cooling sheet, a solution cross-linked product, a rubber sponge, a bearing seal, a lining, an insulating sheet for an automobile, an insulating sheet for an electronic device, a rubber band for a watch, a packing for an endoscope, a bellows hose, a water heater packing/valve, a fender, a fiber non-woven fabric (a protective gear or the like), a base seal material, rubber gloves, a stator of a uniaxial eccentric screw pump, parts for a urea SCR system, a vibration control agent, a vibration suppression agent, a sealant, additives for other materials, and toys.

[Compound]

The compound of the disclosure is represented by Formula (1A).

(1A)

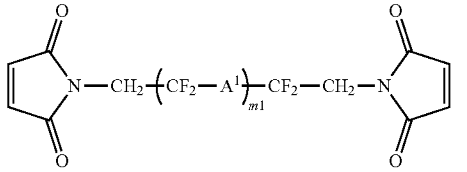

In Formula (1A), m1 is an integer from 0 to 6, and each $A^1$ is independently a single bond or —O—.

It is preferable that the compound represented by Formula (1A) is represented by Formula (1C) described below.

(1C)

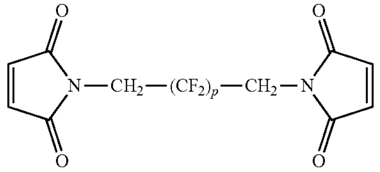

In Formula (1C), p is an integer from 1 to 7. p is preferably 2, 4, or 6, and more preferably 4.

The compound of the disclosure, for example, is manufactured by the following method.

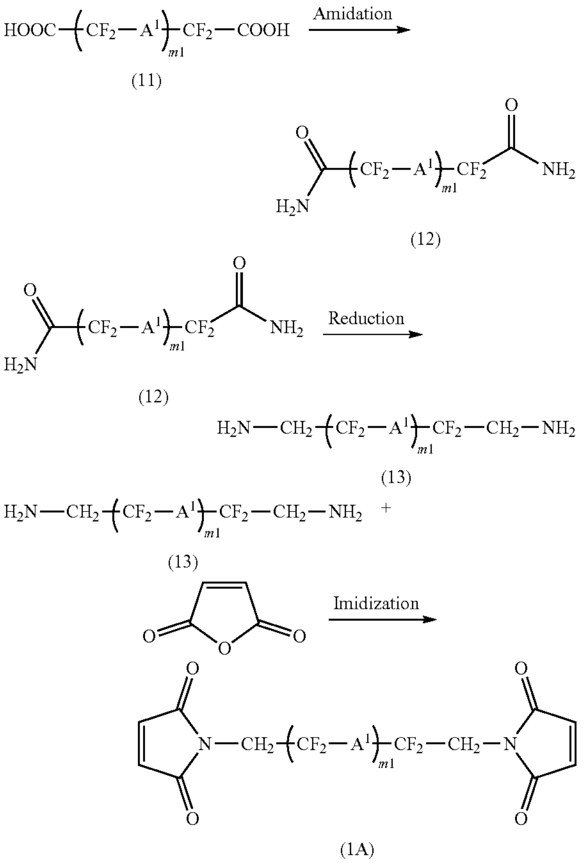

(11)

(12)

(12)

(13)

(13)

(1A)

First, a dicarboxylic acid (11) to be a raw material for manufacturing the compound represented by Formula (1A) is amidated, and diamide (12) is obtained. An amidation method is not particularly limited, and a known method can be used. For example, the dicarboxylic acid (11) is converted to ester or an acid halide, and then, reacts with ammonia, and thus, diamide (12) can be obtained.

Next, the diamide (12) is reduced, and diamine (13) is obtained. A reduction method is not particularly limited, and a known method can be used. For example, in the presence of aluminum chloride, sodium borohydride is used as a reductant, and the diamide (12) is reduced, and then, a hydrochloric acid is added, and thus, a hydrochloride of the diamine (13) is obtained. The hydrochloride of the diamine (13) is neutralized with a base, and thus, the diamine (13) can be obtained. Examples of the base include sodium hydroxide. The diamide (12) may be a commercially available product.

Next, an imidization reaction between the diamine (13) and a maleic anhydride is performed, and the compound represented by Formula (1A) is obtained. An imidization method is not particularly limited, and a known method can be used. For example, the imidization reaction is performed by using a silylation agent and a Lewis acid catalyst. Examples of the silylation agent include 1,1,1,3,3,3-hexamethyl disilazane, chlorotrimethyl silane, methanesulfonic acid trimethylsilyl ester, and N, N'-bis(trimethyl silyl) urea. Examples of the Lewis acid catalyst include zinc chloride, zinc bromide, aluminum halide, tin halide, titanium halide, magnesium halide, and a trifluoroborane etherate complex.

The compound of the disclosure is useful as a cross-linking assistant, in particular, useful as the cross-linking assistant in the cross-linking of the fluorine-containing copolymer.

EXAMPLES

Hereinafter, the disclosure will be described in more detail by Examples; however, the disclosure is not limited to Examples described below unless exceeding the gist thereof.

Example 1

<Manufacturing of Fluorine-Containing Copolymer>

A stainless-steel pressure-resistant reactor vessel that was provided with an anchor blade and had an inner capacity of 20 L was deaerated, and then, 8.2 L of ultrapure water, 733 g of a solution of 30% by mass of $C_2F_5OCF_2CF_2OCF_2COONH_4$ that was an emulsifier, 10 g of $CF_2{=}CFO(CF_2)_3OCF{=}CF_2$ (C3DVE), and 15.9 g of an aqueous solution of 5% by mass of a di sodium hydrogen phosphate 12 hydrate were prepared, and a gas phase was substituted with nitrogen. 198 g of tetrafluoroethylene (TFE) and 454 g of perfluoro(methyl vinyl ether) (PMVE) were pressed into a vessel while stirring with the anchor blade at a rate of 375 rpm, and then, an inner temperature was increased to 80° C. An inner pressure of the reactor vessel was 0.90 MPa [gauge]. 40 mL of an aqueous solution of 1% by mass of ammonium persulfate (APS) was added, and polymerization was initiated. In a case where an addition ratio of monomers to be pressed into the vessel before initiating the polymerization (hereinafter, referred to as "initially added monomers") is represented by a molar ratio, the addition ratio was TFE:PMVE:C3DVE=41.74:57.64:0.62.

TFE was pressed into the vessel at a time point when the inner pressure of the reactor vessel was decreased to 0.89 MPa [gauge] as the polymerization proceeded, and the inner pressure of the reactor vessel was increased to 0.90 MPa [gauge]. By repeating such a procedure, 62 g of PMVE was also pressed into the vessel each time when 80 g of TFE was pressed into the vessel. In addition, 7.0 g of 1,4-diiodoperfluorobutane was pressed into the reactor vessel from an ampule tube, together with 50 mL of ultrapure water, at a time point when 60 g of TFE was pressed into the vessel. An aqueous solution of 3% by mass of APS was added as appropriate, at a point when a polymerization rate was decreased.

The addition of the subsequently added monomers was stopped at a time point when a total added mass of the subsequently added TFE was 1200 g, the inner temperature of the reactor vessel was cooled to 10° C., and a polymerization reaction was stopped. Accordingly, a latex containing a fluorine-containing copolymer was obtained. A polymerization time was 360 minutes. In addition, as the total added mass of each of the subsequently added monomers, TFE was 1200 g and PMVE was 868 g, which were TFE:PMVE=68:32 in terms of a molar ratio.

A nitric acid (Special Grade, manufactured by KANTO CHEMICAL CO., INC.) was dissolved in ultrapure water, and an aqueous solution of 3% by mass of the nitric acid was prepared. The latex was added to the aqueous solution of 3% by mass of the nitric acid, and the fluorine-containing copolymer was aggregated. A solution containing the fluorine-containing copolymer was filtered, washed with ultrapure water, and vacuum-dried at 50° C. and 10 kPa, and thus, a white fluorine-containing copolymer was obtained. The content (a molar ratio) of each constituent unit in the obtained fluorine-containing copolymer was Constituent Unit Derived from TFE/Constituent Unit Derived from PMVE/Constituent Unit Derived from C3DVE=71.40/28.43/0.17. In addition, the content of an iodine atom in the fluorine-containing copolymer was 0.10% by mass. The content of the iodine atom was calculated by a device in which a pretreatment device for an ion chromatograph of an automated sample combustion device (Product Name: "AQF-100", manufactured by Mitsubishi Chemical Analytech Co., Ltd.) and an ion chromatograph were combined.

A filtrate obtained by the filtration performed in a case of obtaining the fluorine-containing copolymer from the latex was filtered with a disk filter, and the obtained liquid was analyzed with an ion chromatograph measuring device, and thus, 3% by mass or more of fluoride ions was not detected with respect to a prepared amount of C3DVE. Accordingly, all C3DVE used for the preparation was polymerized, and the content of a C3DVE unit to all units in the polymer was calculated on the basis of the prepared amount of C3DVE.

<Manufacturing of Fluorine-Containing Compound A1(C4-BMI) Having Two Maleimide Groups>

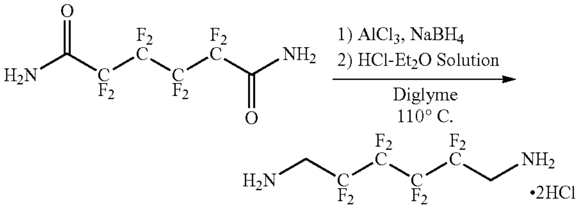

OHDA•2HCl

Diethylene glycol dimethyl ether (332 mL) and aluminum chloride (111) (15.4 g, 115 mmol) were prepared in a 1 L of a four-necked flask provided with a dimroth, in a nitrogen atmosphere, and were stirred for 15 minutes. A reaction liquid was ice-cooled, and a sodium borohydride (13.1 g, 346 mmol) was prepared and stirred for 40 minutes. A suspension (53 mL) of diethylene glycol dimethyl ether of 2,2,3,3,4,4,5,5-octafluorohexane diamide (25.0 g, 86.8 mmol) was dropped into the reaction liquid, and then, stirred for 40 minutes. An outer temperature was 110° C., and stirring was performed for 3 hours. The reaction liquid was cooled at a room temperature, and water (175 mL) was dropped. Next, an aqueous solution (142 mL) of 4.5% by mass of sodium hydroxide was dropped. The reaction liquid was moved to a separating funnel, and diisopropyl ether (623 mL) was added and stirred, and thus, an organic layer 1 was separated. Diisopropyl ether (623 mL) was added to a water phase, and the extraction was performed again, and thus, an organic layer 2 was separated. Diisopropyl ether (623 mL) was added again to the water phase, and the extraction was performed again, and thus, an organic layer 3 was separated. The organic layer 1, the organic layer 2, and the organic layer 3 were combined, and then, dried with anhydrous sodium sulfate, and insoluble matters were removed by filtration under a reduced pressure. The filtrate was ice-cooled, and a diethyl ether solution (175 mL) of 1 mol/L of hydrogen chloride was dropped. 1000 mL of a supernatant liquid was removed by decantation, and then, acetonitrile (541 mL) was added and stirred at a room temperature for 40 minutes. A precipitated solid was collected by filtration under a reduced pressure, and then, dried a reduced pressure at an outer temperature of 50° C., and thus, a 2,2,3,3,4,4,5,5-octafluoro-1,6-hexamethylene diamine hydrochloride (OHDA.2HCl, 22.5 g, 65.5 mmol) was obtained. The structure of OHDA.2HCl was checked by the following data.

$^1$H-NMR (DMSO-d6): δ (ppm) 9.12 (s, 6H), 3.85 (t, 4H, J=17.1 Hz)

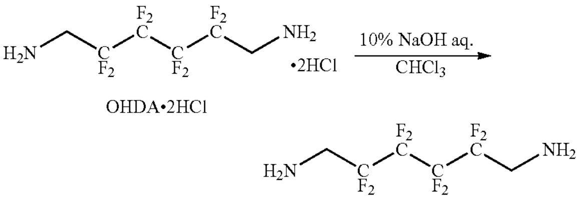

OHDA•2HCl

OHDA

Next, OHDA.2HCl (48.8 g, 142 mmol), chloroform (488 mL), an aqueous solution (488 mL) of 10% of sodium hydroxide were prepared in 2 L of a separating funnel, and stirred, and then, an organic layer was separated. The obtained organic layer was washed with saturated saline (166 mL), and thus, an organic layer was separated. Anhydrous sodium sulfate was added to the organic layer and stirred, and then, insoluble matters were removed by filtration under a reduced pressure. The obtained filtrate was concentrated under a reduced pressure with an evaporator, and thus, 2,2,3,3,4,4,5,5-octafluoro-1,6-hexamethylene diamine (OHDA) was obtained. A yield amount was 33.7 g, and a yield was 90%. The structure of OHDA was checked by the following data.

$^1$H-NMR ($CDCl_3$): δ (ppm) 3.26 (dt, 4H, J=7.68, 15.4 Hz), 1.29 (s, 4H)

$^{19}$F-NMR ($CDCl_3$): δ (ppm) −122 (m, 4F), −124 (m, 4F)

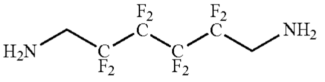

OHDA

+

-continued

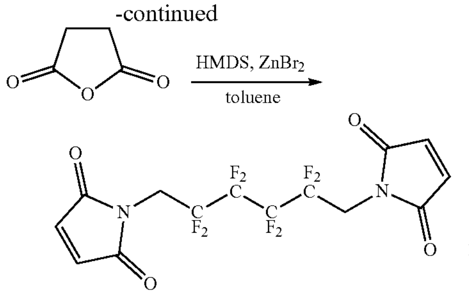

C4-BMI

Next, a maleic anhydride (33.9 g, 346 mmol) and toluene (648 mL) were added to a 2 L of glass flask provided with a dimroth, in a nitrogen atmosphere, and stirred at a room temperature. Next, a solution containing OHDA (30.0 g, 115 mmol) and toluene (408 mL) was added, and then, stirred at an outer temperature of 30° C. for 2 hours. Zinc bromide (78.2 g, 347 mmol) and a toluene solution (168 mL) of 1,1,1,3,3,3-hexamethyl disilazane (76.1 g, 472 mmol) were added to the reaction liquid, and stirred at an outer temperature of 100° C. for 2 hours. The reaction liquid was cooled, and then, 2 mol/L of a hydrochloric acid (500 mL) was added, and insoluble matters 1 were removed by filtration under a reduced pressure. The filtrate was separated, and thus, an organic layer was separated. The obtained organic layer was washed with an aqueous solution (500 mL) of saturated sodium hydrogen carbonate. Dehydration was performed with anhydrous sodium sulfate, and then, the insoluble matters were removed by filtration under a reduced pressure, and thus, the organic layer 1 was obtained. The insoluble matters 1 obtained in advance and ethyl acetate (1000 mL) were prepared in 2 L of a flask, and heated until the inner temperature was 60° C. Cooling was performed at a room temperature, and then, an aqueous solution (500 mL) of saturated sodium hydrogen carbonate was added. After stirring, the organic layer was separated. The obtained organic layer was dehydrated with anhydrous sodium sulfate, and then, the insoluble matters were removed by filtration under a reduced pressure, and thus, the organic layer 2 was obtained. The organic layer 1 and the organic layer 2 were combined and concentrated under a reduced pressure with an evaporator. The obtained concentrate was purified with silica gel column chromatography (Mobile Phase: ethyl acetate), and a crude product of C4-BMI was obtained (39.4 g). Diethyl ether (80 mL) and chloroform (80 mL) were added to the crude product of C4-BMI, heated and refluxed, and then, ice-cooled, and thus, insoluble C4-BMI was collected by filtration under a reduced pressure. A yield amount was 33.5 g, and a yield was 69%. The structure of C4-BMI was checked by the following data.

$^1$H-NMR ($CDCl_3$): δ (ppm) 6.82 (s, 4H), 4.19 (t, 4H, J=15.4 Hz).

$^{19}$F-NMR($CDCl_3$): δ (ppm) −117 (s, 4F), −124 (t, 4F, J=15.3 Hz).

A fluorine content of a compound A1 (C4-BMI) is 22% by atom.

<Manufacturing of Fluorine-Containing Copolymer Composition>

100 parts by mass of the fluorine-containing copolymer described above, 1 part by mass of 2,5-di(tert-butyl peroxy) hexane (Product Name: "PERHEXA 25B", manufactured by NOF CORPORATION), as a cross-linking agent, and 5 parts by mass of C4-BMI described above, as a cross-linking assistant, were mixed, and kneaded with a double roll, and thus, a fluorine-containing copolymer composition 1 was obtained.

<Manufacturing of Cross-Linked Product>

The fluorine-containing copolymer composition was heated and molded at 170° C. for 20 minutes, and thus, a plate-shaped primary cross-linked product having Length of 100 mm×Width of 60 mm×Thickness of 1 mm was obtained. Next, a sheet was heated at 250° C. for 24 hours in a nitrogen atmosphere, and thus, a plate-shaped secondary cross-linked product was obtained.

Example 2

A fluorine-containing copolymer composition 2 was obtained by the same method as that in Example 1, except that the compound A1 (C4-BMI) in Example 1 was changed to a compound A4 (FB-BMI) described below. In addition, a cross-linked product was obtained by the same method as that in Example 1 using the fluorine-containing copolymer composition 2. A fluorine content of the compound A4 (FB-BMI) is 21% by atom.

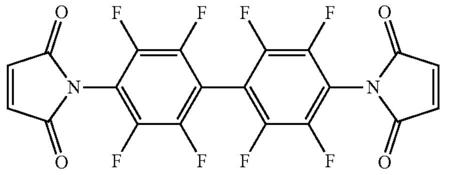

FB-BMI

Example 3

100 parts by mass of the fluorine-containing copolymer described above, 0.5 parts by mass of 2,5-di(tert-butyl peroxy)hexane (Product Name: "PERHEXA 25B", manufactured by NOF CORPORATION), as a cross-linking agent, and 0.5 parts by mass of triallyl isocyanurate (TAIC), as a cross-linking assistant, were mixed, and kneaded with a double roll, and thus, a fluorine-containing copolymer composition 3 was obtained. In addition, a cross-linked product was obtained by the same method as that in Example 1 using the fluorine-containing copolymer composition 3.

Example 4

100 parts by mass of the fluorine-containing copolymer described above, 1 part by mass of 2,5-di(tert-butyl peroxy) hexane (Product Name: "PERHEXA 25B", manufactured by NOF CORPORATION), as a cross-linking agent, and 6 parts by mass of N,N'-1,3-phenylene dimaleimide (BMI), as a cross-linking assistant, were mixed, and kneaded with a double roll, and thus, a fluorine-containing copolymer composition 4 was obtained. In addition, a cross-linked product was obtained by the same method as that in Example 1 using the fluorine-containing copolymer composition 4.

A hardness, a tensile strength, a tensile elongation, and compression set of the obtained cross-linked product were measured. In addition, a vulcanization time in a case of obtaining the cross-linked product was measured. A measurement method is as follows. Measurement results are shown in Table 1. Example 1 and Example 2 correspond to Example, and Example 3 and Example 4 correspond to Comparative Example.

(Hardness)

A plate-shaped cross-linked product (a thickness of 1 mm) was punched out with a No. 4 dumbbell to prepare three test pieces. A hardness (Shore-A) was measured by a type A durometer, on the basis of JIS K6253-3:2012, by using the prepared test piece. A test was implemented by using three test pieces, and a value in which measured values of three test pieces were arithmetically averaged was recorded.

As a measuring device, an automated hardness tester for a rubber (Product Name: "DIGI TEST", manufactured by Bareiss Prufgeratebau GmbH) was used.

(Tensile Strength and Tensile Elongation)

A plate-shaped cross-linked product (a thickness of 1 mm) was punched out with a No. 4 dumbbell to prepare three test pieces. A tensile strength and a tensile elongation were measured on the basis of JIS K6251:2010 (corresponding International Standard ISO 37:2005), by using the prepared test piece. Each test was implemented by using three test pieces, and a value in which measured values of three test pieces were arithmetically averaged was recorded.

As a measuring device, a tensile tester with data processing (Product Name: "QUICK READER TS-2530", manufactured by Ueshima Seisakusho Co., Ltd.) was used.

(Compression Set)

Three O-ring test pieces of P26 were prepared on the basis of JIS B 2401-1:2012. The prepared test pieces were used, and each compression set (%) in a case of being retained at 250° C. for 70 hours, 168 hours, and 336 hours was calculated on the basis of JIS K 6262:2013. The compression set was calculated on the basis of the following expression. The test was implemented by using three test pieces, and a value in which values calculated by three test pieces were arithmetically averaged was recorded. As the compression set is close to 0%, recovery properties of the cross-linked product are excellent, that is, the cross-linked product is favorable in cross-linking.

Compression Set (%)=(Original Thickness of Test Piece−Thickness in 30 Minutes after Taking out Test Piece from Compression Device)÷(Original Thickness of Test Piece−Thickness of Spacer)×100

(Vulcanization Time)

The fluorine-containing copolymer composition was heated at 170° C. for 20 minutes. A 2% vulcanization time (t2) and a 90% vulcanization time (t90) were measured. A cross-linking rate is high as t2 and t90 are small.

As a measuring device, a dynamic viscoelastic device (Product Name: "RPA2000", manufactured by Alpha Technologies) was used.

TABLE 1

| | | Example 1 | Example 2 | Example 3 | Example 4 |
|---|---|---|---|---|---|
| Fluorine-containing copolymer (parts by mass) | | 100 | 100 | 100 | 100 |
| Cross-linking agent (parts by mass) | | 1 | 1 | 0.5 | 1 |
| Cross-linking assistant (parts by mass) | TAIC | 0 | 0 | 0.5 | 0 |
| | C4-BMI | 5 | 0 | 0 | 0 |
| | FB-BMI | 0 | 5 | 0 | 0 |
| | BMI | 0 | 0 | 0 | 6 |
| Physical properties | Hardness | 73 | 79 | 69 | 79 |
| | Tensile strength (MPa) | 19.4 | 8.3 | 28.1 | 20.1 |

TABLE 1-continued

| | | Example 1 | Example 2 | Example 3 | Example 4 |
|---|---|---|---|---|---|
| | Tensile elongation (%) | 187 | 199 | 240 | 171 |
| Compression set (%) | 250° C. 70 hr | 64 | 70 | 88 | 46 |
| | 250° C. 168 hr | 81 | 83 | 112 | 64 |
| | 250° C. 336 hr | 90 | 95 | — | 83 |
| Vulcanization time (minutes) | t90 | 1.1 | 15 | 1.2 | 4.4 |
| | t2 | 0.6 | 0.7 | 0.3 | 0.4 |

As shown in Table 1, in Example 1 and Example 2, it was found that the compression set in a case of being retained at 250° C. for 70 hours was small, and the vulcanization time was also short.

However, in Example 3 using TAIC as the cross-linking assistant, the compression set in a case of being retained at 250° C. for 70 hours was large. In addition, in Example 4 using BMI as the cross-linking assistant, the vulcanization time was long.

Note that, the disclosure of Japanese Patent Application No. 2020-028034 filed on Feb. 21, 2020 is incorporated herein by reference in its entirety. In addition, all documents, patent applications, and technical standards described herein are incorporated in the specification by reference to the same extent as a case where it is specifically and individually stated that the individual documents, patent applications, and technical standards are incorporated by reference.

What is claimed is:

1. A fluorine-containing copolymer composition, comprising:

a fluorine-containing copolymer; and a fluorine-containing compound having two maleimide groups of Formula (1):

(1)

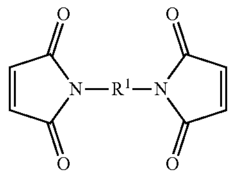

wherein $R^1$ is represented by Formula (X):

(X)

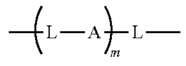

m is an integer from 0 to 8, where when m is 0, L is a fluorinated alkylene group having from 1 to 30 carbon atoms, a fluorinated cycloalkylene group having from 3 to 20 carbon atoms, or a perfluoroarylene group having from 5 to 20 carbon atoms, and when m is 1 or more, each L is independently an alkylene group having from 1 to 30 carbon atoms, a cycloalkylene group having from 3 to 20 carbon atoms, an arylene group having from 5 to 20 carbon atoms, a fluorinated alkylene group having from 1 to 30 carbon atoms, a fluorinated cycloalkylene group having from 3 to 20 carbon atoms, or a perfluoroarylene group having from 5 to 20 carbon atoms, at least one of a plurality of Ls is a fluorinated alkylene group having from 1 to 30 carbon atoms, a fluorinated cycloalkylene group having from 3 to 20 carbon atoms, or a perfluoroarylene group having from 5 to 20 carbon atoms, and each A is independently a single bond or —O—, and wherein the fluorine-containing copolymer comprises a copolymerized monomer having at least one fluorine atom and two polymerizable unsaturated groups.

2. The fluorine-containing copolymer composition according to claim 1, wherein a shortest path that links the nitrogen atoms of the two maleimide groups of Formula (1) comprises from 3 to 9 atoms.

3. The fluorine-containing copolymer composition according to claim 1, wherein a fluorine atom content of the compound of Formula (1) is from 3% by atom to 32% by atom.

4. The fluorine-containing copolymer composition according to claim 1, wherein the compound of Formula (1) is represented by Formula (1A) or Formula (1B):

(1A)

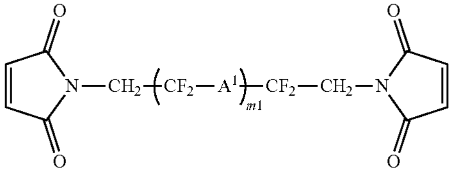

(1B)

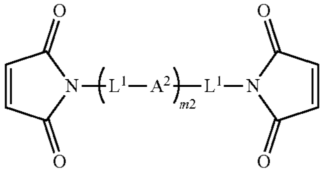

wherein m1 is an integer from 0 to 6, and each $A^1$ is independently a single bond or —O—, and m2 is an integer from 0 to 4, each $L^1$ is independently a perfluoro-o-phenylene group, a perfluoro-m-phenylene group, or a perfluoro-p-phenylene group, and each $A^2$ is independently a single bond or —O—.

5. The fluorine-containing copolymer composition according to claim 1, wherein the compound of Formula (1) is represented by Formula (1C) or Formula (1D):

(1C)

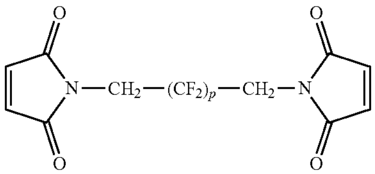

-continued (1D)

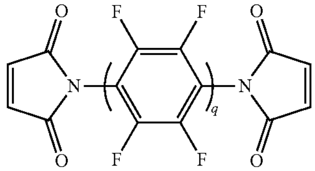

wherein p is an integer from 1 to 7, and q is an integer from 1 to 5.

6. The fluorine-containing copolymer composition according to claim 1, wherein a ratio of a content of the compound of Formula (1) to a content of the fluorine-containing copolymer is from 0.01 to 0.1 on a mass basis.

7. The fluorine-containing copolymer composition according to claim 1, wherein the fluorine-containing copolymer further comprises:

an iodine atom;

a constituent unit derived from tetrafluoroethylene; and a constituent unit derived from a perfluoroalkyl vinyl ether.

8. A cross-linked product formed by cross-linking the fluorine-containing copolymer composition according to claim 1.

9. A compound represented by Formula (1A):

(1A)

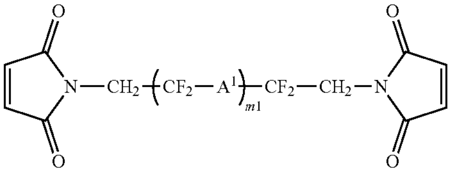

wherein m1 is an integer from 0 to 6, and each $A^1$ is independently a single bond or —O—.

10. The compound according to claim 9, wherein the compound represented by Formula (1A) is represented by Formula (1C):

(1C)

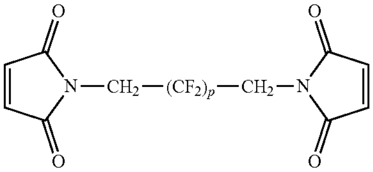

wherein p is an integer from 1 to 7.

11. The compound according to claim 10, wherein p is 2, 4, or 6.

* * * * *